United States Patent [19]

Tanyolac et al.

[11] Patent Number: 4,563,893
[45] Date of Patent: Jan. 14, 1986

[54] METHODS AND APPARATUS FOR DETECTION AND IDENTIFICATION OF VOLATILE MATERIALS AND ODORS

[75] Inventors: Necmi Tanyolac, Bogazici University, Istanbul, Turkey; John N. Labows, Horsham, Pa.

[73] Assignee: Necmi Tanyolac, Istanbul, Turkey

[21] Appl. No.: 487,870

[22] Filed: Apr. 22, 1983

[51] Int. Cl.$^4$ ............................................. G01N 31/06
[52] U.S. Cl. ........................................ 73/23; 324/61 R
[58] Field of Search ....................... 73/23; 324/61 R; 422/88, 90, 98; 436/149, 151

[56] References Cited

U.S. PATENT DOCUMENTS

| | | | |
|---|---|---|---|
| 2,741,912 | 4/1976 | Schultze | 73/23 |
| 2,837,912 | 6/1958 | Moncrieff | 73/23 |
| 3,558,279 | 1/1971 | McRae et al. | 422/90 |
| 4,399,687 | 8/1973 | Collins | 73/23 |
| 4,411,156 | 10/1983 | Lowe | 73/23 X |

FOREIGN PATENT DOCUMENTS

| | | |
|---|---|---|
| 1673104 | 2/1974 | Fed. Rep. of Germany . |
| 499106 | 12/1970 | Switzerland . |
| 1105641 | 3/1968 | United Kingdom . |

OTHER PUBLICATIONS

"The Chemistry of Aroma", Parliament Chemtech, vol. 9, pp. 284–289 (1980).
Zlatkis, "The Role of Organic Volatile Profiles in Clinical Diagnosis", Clinical Chemistry, vol. 27, pp. 789–797 (1981).
Labows et al., "Head Space Analysis of Volatile Metabolites of Pseudomonas Aeruginosa and Related Species by Gas Chromatography–Mass Spectrometry", Journal of Clinical Microbiology, pp. 521–526 (1980).
Tanyolac, "The Electro–Odocell for Inspection and Grading of Meat and Fish", Olfaction and Taste II, Proceedings of 2nd International Symposium, Tokyo, Sep. 1965, pp. 609–623, Pergamon Press (1967).
Meuire et al., "Determination of Trace Organics in Air and Water", Journal of Chromatagraphic Science, vol. 11, pp. 559–570 (1973).
Kostelc et al., "Salivary Volatiles as Indicators of Periodontitis", Journal of Periodontal Research, vol. 15, pp. 1185–1192 (1980).
Tanyolac, "Modern Theories of Odor and Olfaction and Objective Olfactometry", Excerpta Medica International Congress Series No. 206-Oto-Rhino-Laryngology, Proceedings of the 9th International Congress, Mexico, D.F. 8/10-14/69.
Tanyolac, "The Electro–Odocell for Odor Measurement and Surface Effects", Surface Effects in Detection, pp. 89–100, Spartan Books (1965).
Tanyolac, "Electro–Odocell and Theories of Odor", Theories of Odor and Odor Measurement, pp. 537–561, Technivision (1968).

Primary Examiner—Herbert Goldstein
Attorney, Agent, or Firm—Woodcock Washburn Kurtz Mackiewicz & Norris

[57] ABSTRACT

An apparatus for the detection of odor has a dielectric sensor having a dielectric potential responsive to absorbed odor molecules, carrier gas flow for directing a substantially uniform flow of carrier gas into contact with the sensor and a detector for detecting the dielectric potential of the sensor. In accordance with certain preferred embodiments, the sensor is at least partially permeable to the flow of the carrier gas. Methods for detection of odors employing apparatus of this invention are also disclosed. Thus, in accordance with a preferred embodiment, known and unknown samples are entrained into the carrier gas for contact with the dielectric sensor. A curve of the dielectric potential of the sensor taken over a period of time for each of the samples is prepared and the curves compared to determine the identity and concentration of the odors.

24 Claims, 6 Drawing Figures

METHODS AND APPARATUS FOR DETECTION AND IDENTIFICATION OF VOLATILE MATERIALS AND ODORS

BACKGROUND OF THE INVENTION

This invention relates to methods and apparatus for the detection and identification of volatile materials, especially odors. For the purposes of the present specification, an odor is a material in a gaseous or volatile state either in a native, gaseous condition or in a form which has been given off or released by a solid or a liquid. Many such odorous, volatile materials are detectable by sensation by one or more animals, especially mammals, including humans. For convenience, however, odors, as contemplated by the present invention, include not only those volatile materials which are capable of being sensed by humans or other mammals but also those which are capable of being detected through the employment of one or more embodiments of the present invention.

Numerous methods have been proposed for the detection of odor. See in this regard, "Modern Theories of Odor and Olfaction and Objective Olfactometry", Tanyolac, Excerpta Medica, International Congress Series No. 206-OTO-RHINO-LARYNGOLOGY; *Proceedings of the 9th International Congress*, Mexico D.F., Aug. 10-14, 1969. Thus, it has been known to employ thermal, colorimetric determinations for the detections of certain toxic leaks. A "stinkometer" was developed in 1945 comprising a wet chemical colorimetric determination for determining the putrefaction of fish. Additionally, on Odocell developed in 1949, has also been employed to detect odor. The Odocell used the effect of odor-containing air on the surface tension of liquids to determine the presence and characteristics of odors.

As further reported in the proceedings in the 9th International Congress paper by Tanyolac, an electrochemical means for the determination of odors employing an electrolytic solution has also been reported as has a contact-potential olfactometer based upon the change of contact potential along various solid surfaces.

Yet another attempt at detection of odor has relied upon the changes in temperature of a film due to adsorption of odorous vapors thereupon. A thermistor coated with certain films is used as a sensing element for detecting such changes in temperature.

A further prior approach to the detection of odor is the Electro-Odocell. This device and method is reported, for example, in Great Britain Pat. No. 1,105,641 dated Mar. 6, 1968 in the name of Tanyolac and Gultekin, together with foreign language counterparts thereof including Swiss Pat. No. 499,106 and West German Pat. No. 1,673,104. This Electro-Odocell is also reported in the proceedings of the 9th International Congress paper referred to previously. It is also discussed in "The Electro-Odocell for Odor Measurement and Surface Effects", Tanyolac, *Surface Effects in Detection*, pp. 89-100, Spartan Books (1965); "Electro-Odocell and Theories of Odor", Tanyolac, *Theories of Odor and Odor Measurement*, pp. 537-561, Technivision (1968); and "The Electro-Odocell for Inspection and Grading of Meat and Fish", Tanyolac, *Olfaction and Taste II, Proceedings of the 2nd International Symposium, Tokyo, September,* 1965, pp. 609-623, Pergamon Press (1967).

The static Electro-Odocell provides for the static detection of odor by exposing a dielectric material to odor molecules and detecting the resulting changes in surface potential as adsorption of the molecules occurs. The maximum value of surface potential is related to adsorption of the maximal amount of odor molecules, taken in sum, on the dielectric sensor. While an initial transient, representing a value of approximately 10% of the final potential, may be detected within a few seconds, the final values require substantially longer to ascertain. This static Electro-Odocell is cumbersome to employ and requires a lengthy period of purging of odor molecules from the dielectric surface between uses.

SUMMARY OF THE INVENTION

In accordance with the present invention, apparatus is provided for the detection of odor, comprising dielectric sensing means having a dielectric potential responsive to adsorbed odor molecules, together with carrier gas flow means for directing a substantially uniform flow of carrier gas into contact with the sensor means, and means for detecting the dielectric potential of the sensing means. In accordance with a preferred embodiment, the sensing means is at least partially permeable to the flow of carrier gas and at least a portion of the gas flow occurs via permeation of the sensing means. Means for holding samples in such a fashion that odor molecules comprising, emanating from, or associated with the samples may be entrained in the gas flow are also contemplated hereby. In accordance with yet another preferred embodiment, the gas flow means comprises means for applying a vacuum downstream from the sensing means.

The present invention also contemplates methods for detecting odor comprising contacting a dielectric sensing means having a dielectric potential sensitive to the adsorption of odor molecules thereupon, with a substantially uniform flow of carrier gas, and detecting the dielectric potential of the sensing means. In accordance with other preferred embodiments, the dielectric potential is displayed or collected digitally as a function of time; the shape of the potential-time curve may be related to certain properties of the odor molecules tested. In a still more preferred embodiment, one or more odiferous materials are detected by the apparatus of the present invention in accordance with the methods of the present invention to form a detection curve of each of said known materials. One or more sample, unknown materials are then detected in accordance with this invention and the resulting detection curve compared with those of the known species.

For the purposes of the present specification, the term dielectric potential is used instead of surface potential referred to in connection with the prior static Electro-Odocell. Dielectric potential is the potential measured across an odor sensing dielectric membrane. This voltage is related to changes in surface potential, change in dielectric constant and change of resistivity of the sensing membrane due to molecules collected or adsorbed on the surface and in the pores of the membrane.

The methods and apparatus of the present invention are well adapted for use in detecting spoilage in meat, fish and other animal products, deterioration in grain and other foodstuffs, analysis of soil samples for various properties such as pesticidal and other contamination, and other widely varying determinations based upon the presence or absence of odor molecules, comprising, emanating from, or associated with a sample. In a particularly preferred embodiment, the methods and apparatus of the present invention are employed in detecting one or more states of being of a mammal. Thus, a body cavity of a mammal may be considered to be a "head space" for the collection of a vaporous or gaseous sample suspected of containing odor molecules. The presence or absence of certain types of odor molecules in such spaces, as detected in accordance with the present invention, may be definitive of certain bodily states such as, for example, estrus, or periodontal disease. It is also contemplated that samples of tissue or body fluids or of vegetable matter may be collected and the vaporous constituents or by-products emanating therefrom be detected in accordance with this invention in order to provide certain indications as to, for example, metabolic and/or disease states associated with such samples.

OBJECTS OF THE INVENTION

It is a principle object of this invention to provide apparatus for the rapid dynamic detection of odors.

Yet another object of this invention is to provide apparatus for the detection of odor employing dielectric sensing means in contact with a substantially uniform flow of carrier gas.

Yet another object of this invention is to provide odor detection apparatus employing dielectric sensing means which is at least partially permeable to the flow of gas.

A still further object of this invention provides odor detecting apparatus including means for entraining in a flow of gas for contact with a dielectric sensing means, vaporous material comprising, associated with, or emitted from a sample to be tested.

Methods for identifying odors are other principle objects of this invention. Thus, such identification is accomplished in accordance with an object of the invention, by contacting a dielectric sensing means with a substantially uniform flow of carrier gas and detecting the dielectric potential produced by the sensing means.

A further object introduces or entrains into the flow of gas a vaporous sample, comprising, associated with, or emitted by a sample to be tested. A still further object of the invention identifies odor by comparing the detection curve of the dielectric sensing means of an unknown sample suspected to contain odor with one or more curves of previously tested, known odiferous samples.

A still further object is to test foodstuffs for putrefaction or spoilage.

An additional object is to determine the status of a mammal by monitoring head space vapors present in a body orifice of the animal or by monitoring vaporous products emitted by tissue or fluid samples of an animal or vegetable material.

Still further objects will become apparent from a review of the present specification.

A still further object is to test pollutants in the air, in water and in soil.

DETAILED DESCRIPTION OF THE INVENTION

Figure 1:
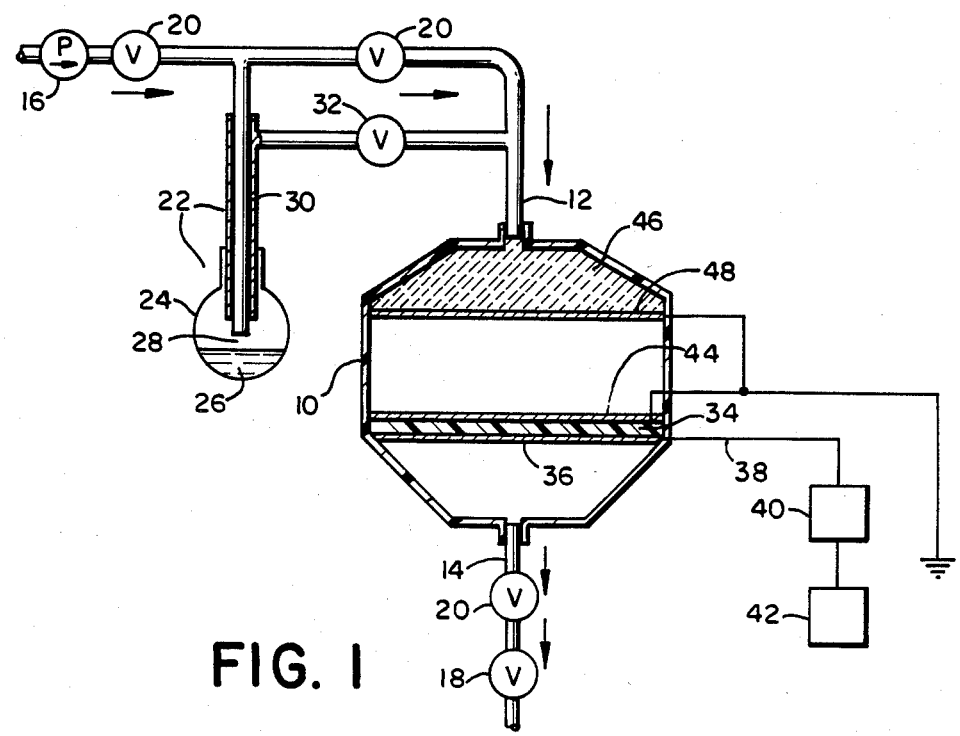
FIGS. 1 and 2 depict apparatus for detecting odor in accordance with certain embodiments of this invention.
Figure 2:
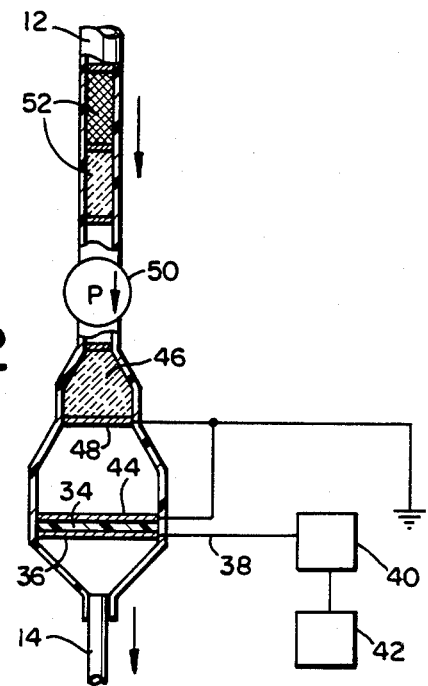

An exemplary apparatus for the detection of odor is presented in FIG. 1. A housing 10 is provided having a gas inlet 12 and a gas outlet 14. The gas inlet 12 and/or gas outlet 14 are provided with means for causing a substantially uniform flow of the carrier gas to transit the housing 10. Such carrier gas flow means may comprise either a pressurizing system such as is suggested schematically at 16 and/or means for applying a partial vacuum 18 at the gas outlet 14. Suitable valving means 20 are also provided so as to regulate and properly direct the flow through the housing 10 to provide a substantially uniform flow of carrier gas in terms of composition, pressure and flow rate therethrough. The gas may be any gas having an effect upon the dielectric cell which does not interfer with detection of odorous materials. Thus, air, nitrogen, helium etc. may be employed as may a wide variety of other gases and gas mixtures.

In accordance with certain preferred embodiments, there is also provided entrainment means 22 for entraining in the gas flow a vaporous sample material comprising, associated with, or emitted by a sample. In the embodiment of FIG. 1, the entrainment means 22 comprises a sample container 24 adapted for containment of a sample 26 to be analyzed. The head space of the sample container 28 will, thus, either contain the sample if the sample is gaseous, or become the repository for vaporous emission or association products of a solid or liquid sample. Perfusion means 30 are also provided for directing at least a portion of the flow of gas through the head space 28 thus to entrain vaporous materials contained in said head space into the flow of gas transitted to the housing 10. Suitable valving, shown schematically 32, is also provided to facilitate this entrainment and to assist in the regulation of gas flow through the housing.

The flow of carrier gas through the housing 10 is performed in such a way as to contact a dielectric sensing means 34. In accordance with a preferred embodiment, the dielectric sensing means 34 is at least partially permeable to the flow of the carrier gas and at least a portion of said flow is caused to permeate the sensing means 34. It is also possible, however, to arrange the dielectric sensing means 34 in the housing 10 in such a fashion that the flow of carrier gas is directed upon the sensing means 34 but is not caused necessarily to permeate it. It is preferred that the dielectric sensing means 34 be supported by, for example, a conductive support means 36. It is desired, in accordance with preferred embodiments of this invention, to provide conductive support means 36 which is at least partly permeable to the flow of carrier gas. The conducting support means 36 must then be amenable to such flow. In such a case, the support means 36 may comprise a perforate sheet, wire mesh, or similar structure. The dielectric sensing means 34 is provided with electrical contact means 38 in electrical contact either directly or via the conductive support means 36 with a dielectric potential detecting means 40. Such potential detecting means 40 may comprise, for example, an electrometer, volt meter, picoammeter, or other means for detecting electrical potential. In the alternative, the potential detecting means 40 may comprise a preamplifier together with a recording device for graphically illustrating the change in potential at the dielectric sensing means 34 with time.

The potential detecting means 40 may be caused directly to record the value of the dielectric potential at the dielectric sensing means 34, either graphically or otherwise. Alternatively, it may be connected electrically to digitizing means 42 which may comprise an electronic digitizer, a general purpose digital computer, or other means for collecting and storing digitized data for analysis.

The odor detecting apparatus of the present invention preferably also comprises an electrical grounding means 44 for providing a source of reference, ground potential to detection means 40. The grounding means 44 and conductive means 36 must be electrically insulated from each other such as by employing a non-conducting plastic as housing 10. The grounding means 44 must not impede the flow of carrier gas to sensing means 34.

In accordance with certain preferred embodiments of this invention, there is also provided means for removing certain molecules from the gas stream prior to its impingement upon the dielectric sensing means 34. Thus, one or more gas scrubbing chambers 46 may be provided generally up flow as regards the flow of the gaseous carrier from the dielectric sensing means 34. In the embodiment illustrated in FIG. 1, a gas scrubbing chamber 46, is formed in the housing 10 by employment of a perforate or mesh screen 48. It may be filled with various absorbent media which are capable of irreversibly removing from the carrier gas flow certain undesirable or interfering molecules. It is preferred that screen 48 also be grounded. The gas scrubbing chamber 46 may contain any of a wide variety of absorbent media for removing low molecular weight molecules from the gas stream. In accordance with a preferred embodiment, the scrubbing chamber contains desiccant material such as molecular sieves, silica gel or the like. It is also possible to use a multi-component material in the scrubbing chamber which is capable of removing molecules in addition to water. Thus, molecular sieves capable of removing small molecular weight alcohols, amines, etc. from the gas stream may be so employed. As will be apparent to those skilled in the art different dielectric sensing means 34 may be responsive to different odor molecules in different degrees. Thus, it may be possible to match the contents of gas scrubbing chamber 46 with differing dielectric sensing means so as to provide enhanced response for certain classes and types of odor molecules. It is also possible to employ in the gas scrubbing chamber 46 certain materials which are capable of removing certain components of the gaseous flow such as nitrogen, carbon dioxide, sulfur dioxide, and hydrogen sulfide. This removal may enable the dielectric sensing means to exhibit increased sensitivity of larger molecules having lesser individual effect upon the change in dielectric potential of the sensing means. In this regard, it is frequently desirable to employ molecular sieves to remove water and certain other materials such as low molecular weight alcohols and amines prior to contacting the dielectric sensing means with the gas flow. Adsorbants capable of removing certain of the foregoing and other species from gas flows are well known to those skilled in the art who will be easily able to determine the desirability of removing any particular low molecular weight composition from the gas flow in any given experimental circumstance.

Alternative locations for the gas scrubbing chamber 46 is also contemplated by the present invention. Thus, one or more gas scrubbing chambers may be located generally upstream from the dielectric sensing means 34 as regards the flow of the carrier gas. Such chambers may, for example, also be placed upstream from the entrainment means 22 so as to pretreat the carrier gas prior to entrainment of a vaporous sample.

In accordance with other embodiments of the present invention, entrainment means 22 may comprise a wide variety of devices for entraining a vaporous materials comprising either a sample or a vapor associated with or emanated by a sample in the flow of carrier gas. One preferred embodiment perfuses a sample chamber contained within a penetrometer designed for penetration of earth. Analysis of the vaporous products collection in the sample chamber such as those indicative of the presence of pollutants, may thus be accomplished. It is also preferred to locate the housing 10, dielectric sensing means 34 and potential detecting means 40 inside of the penetrometer.

It is also preferred to obtain direct entrainment of gases from body cavities of certain mammalian animals, especially when the substantially uniform carrier gas flow is accomplished through the application of a vacuum by a vacuum source 18 to the gas outlet 14. In this way, the gas inlet 12 may be directly in communication with a body cavity of an animal for evaluation of the volatiles contained therein. Additionally, biological samples such as tissue, bodily fluids, or vegetable matter may be placed in sample container 24 and the head space volatiles entrained in the gas flow.

In accordance with yet another embodiment, it is possible to concentrate small amounts of volatile materials and to entrain the concentrated vaporous materials into the gas flow for analysis. Concentration of such materials on, for example, certain polymeric support media such as TenaxÅ trademark of the Akzo Company, may be preferred for the detection of relatively weak or dilute odors. Adsorption of such weak or dilute odors onto carbon, other adsorption media, capture in a cryogenic trap, or other concentration schemes may also be accomplished in accordance with the spirit of this invention.

FIG. 2 illustrates another embodiment of the present invention. The gas flow means is provided by an in line pump 50 upstream from the dielectric means 34. In addition to gas scrubbing chamber 46 separated from the dielectric means 34 by screen 48 as depicted in FIG. 1, the embodiment depicted in FIG. 2 further comprises additional scrubbing chambers 52 which may contain additional materials for removal of certain low molecular weight volatiles from the gas flow stream such as water and interferent species. In an alternative embodiment, a source of vacuum may be applied to gas outlet 14 in lieu of pump 50 to produce a substantially uniform flow of gas from the gas inlet 12 through the housing 10, across or through the dielectric means 34 and out the gas outlet 14. The apparatus of FIG. 2 is particularly adapted for the sampling of head space vapors in, for example, a mammalian body space, an agricultural product in travelers' baggage or pollution in air.

In accordance with the preferred practice of the present invention, the odor detecting apparatus may comprise a plurality of sensing means 34. As discussed hereinbefore, the dielectric sensing means 34 are preferably constructed as to be at least partially permeable to the passage of gas flow therethrough. Accordingly, it is preferred that the apparatus be constructed such that substantially permeation of the dielectric sensing means by the gas flows occurs in use. As will be apparent to those skilled in the art, such permeation will increase the effective surface area of the dielectric sensing means, the change in the dielectric constant of the membrane and the resistivity of the membrane. Improved sensitivity and accuracy of detection response results.

In accordance with the practice of this invention, the dielectric sensing means 34 is best characterized as being a material having a dielectric potential responsive to the adsorption of odor molecules thereupon. Any dielectric material which is responsive to the presence of such odor molecules adsorbed onto one or more surfaces of the material may be suitably employed in the practice of this invention. Such materials may comprise, for example, various inorganic materials including glasses, mica, dielectric crystalline material, plastics and a wide variety of other organic and inorganic materials. Such dielectric sensing means are preferably fabricated from a wide variety of organic polymers including both natural and synthetic polymers. Examplary polymers which may be so employed include celluloses, cellulose acetate, cellulose nitrate, polyacrylonitrile, polyvinylidene fluoride, polyfluorohydrocarbons, orlon, nylon, polysulfone, and a wide variety of other materials capable of exhibiting a change in dielectric potential upon adsorption of odor molecules thereupon.

The mechanism of action of the adsorption of odor molecules on one or more surfaces of a dielectric material has been proposed previously. In this regard, reference should be had to those patents and publications referred to previously in this specification relating to the static Electro-Odocell of Tanyolac, which materials are incorporated herein by reference. While not intending to be bound by any particular theory concerning the mechanism of operation of dielectric sensing means in connection with the practice of this invention, it is believed that changes in the dielectric potential of such means upon the adsorption of odor molecules thereupon may be viewed as resulting in changes in surface potential, dielectric constant and resistivity of the sensing membrane. It is believed that whether the molecules of the dielectric material are polar or non-polar, the net effect of an external field upon the materials is similar. Thus, it is believed that there will be a thin layer of bound charge on the surface of the dielectric material due to the adsorption effect of adsorbed odor molecules. The odor molecules to be detected may be either polar or non-polar in accordance with this theory. Presence of an electric field at the surface of the dielectric material due to gas molecules being adsorbed thereupon will induce a dipole even upon initially non-polar odor molecules. It is also believed that the potential of the dielectric surface will be reduced or increased depending upon the molecular orientation of the adsorbed odor molecules. Thus, the view is held that intramural effects among groups of odor molecules when adsorbed upon a particular dielectric surface will be reflected in the dielectric potential generated therein. It is accordingly believed that different odor molecule types or classes will be adsorbed differently upon different dielectric surfaces and will give rise to different dielectric potentials upon such adsorption. In practice, it may be convenient to "tailor" the identity of the dielectric material to the types or classes of odor molecules to be detected.

In accordance with the practice of the methods of the present invention, a dielectric sensing means having a dielectric potential which is sensitive to the presence of odor molecules adsorbed onto it is contacted with a substantially uniform flow of carrier gas and the dielectric potential of the sensing means is detected. Vaporous materials comprising, emanating from, or associated with a sample are preferably entrained into the carrier gas flow for subsequent contact with the dielectric detecting means. Passage of the carrier gas containing the vaporous material to be detected through one or more means for the adsorption of low molecular weight materials as hereinbefore described is preferably accomplished prior to contact with the detecting means in accordance with the practice of the methods of this invention.

The detection of changes in dielectric potential in dielectric sensing means in accordance with the present invention may be easily accomplished through the employment of potential detecting means in electrical contact with one surface of the dielectric sensing means. The detecting means may comprise a volt meter, picoammeter, electrometer, preamplifier, or any other means for detecting changes in such potential. It is preferred that such detecting means be electrically in communication with a means for storing and/or displaying the data thus collected. Thus, the potential data may be digitized and stored for analysis, displayed graphically, or otherwise presented for evaluation. The data thus gathered may be seen to comprise a data curve of potential versus time. The curve may either be an actual, graphic curve or may be digitized representation curve.

Unlike the static methods for the detection of odors known to the prior art, the present, dynamic methods are more suitable to the rapid detection and accurate identification of odors. Such prior methods detect the changes in the surface potential of a dielectric sensing means as adsorbtion of odor molecules onto the sensing means occurs through diffusion in the vicinity of the sample. The shortcomings of this method include inadequacy of the resulting data from which accurate inferences as to the nature and quality of the subject odor may be determined together with lack of rapidity in making the odor determination.

The present method provides a dynamic method for determining odor wherein a carrier gas having a substantially uniform composition and flow rate is caused to contact the dielectric sensing means. Upon the entrainment of vaporous odor molecules into the carrier gas, dynamic adsorption and, preferably, permeation and adsorption of such molecules onto and from the dielectric sensing means is accomplished. It is believed that different odor molecules will adsorb, permeate and desorb onto particular dielectric materials with differing rate constants depending upon their nature and upon the identity of the dielectric membrane. Accordingly, the change in the dielectric potential on account of the adsorption and permeation of such materials will vary with their identity and quantity. For an odor comprising a plurality of diverse molecular odorant species, the resulting changes in dielectric potential of the sensing means will comprise, to a first approximation, a sum of the individual potential changes of individual molecular specie adsorptions. Additionally, it is believed that intramolecular effects among differing classes and types of odorant molecules may also exist causing secondary perturbations of the overall potential changes demonstrated by the dielectric sensing means. In sum, it is believed that the dynamic process thus envisioned will provide much more information from which identity of odorant materials may be determined. At the same time, the dynamic process is such that far more rapid determination of odorant concentration and identity may be made than is possible employing the prior art, static methods since adsorption is facilitated by the gas flow.

In accordance with preferred methods, a vaporous material comprising, associated with, or emitted by a sample is entrained in the gas flow of an equilibrated detection apparatus. Detection of the dielectric potential of the dielectric sensing means is conducted preferably from a period of time at least just prior to the entrainment of the vaporous material until subsequent to a substantial dissipation of the sample from the dielectric means. If the data is displayed graphically, the resulting curve of dielectric potential with time will generally not be straight; it will be generally possessed of a shape indicative of the nature of the odor detected. By entraining a plurality of vaporous materials of known composition in a particular dielectric cell or in a dielectric cell having known properties, and by comparing their shape and magnitude with those of subsequent potential versus time curves collected in connection with the detection of unknown samples, the identity and relative quantity of the unknown samples may be determined.

As has been suggested, comparison of data curves in graphic form may be conveniently accomplished using informal curve fitting accomplished by human observation and analysis. It is also possible, and in some cases preferrred, to employ digitizing means to represent the potential data curves collected over time. Such digitized curves data may then be subjected to analysis employing a general purpose digital computer. Comparison of digitized data from known and unknown samples by computerized curve fitting may then take place in a convenient fashion to assign identities to the unknown materials.

The shape of a curve representing dielectric potential as a function of time is preferably evaluated during both the adsorption and desorption of odor molecules from the surfaces of a dielectric sensing means. The response time, rate of rise, maximum value, rate of decline, and general shape of the curve for both adsorption and desorption are all indicative of the nature, types and classes of odor molecules detected, together with their amounts. The area under the adsorption and desorption curves is a further characteristic of the odor of the samples tested.

The methods and apparatus of the present invention are particularly useful for analysis of odors in situations where it is desirable to know the presence or absence of a suspected odorous material. By inference, the presence or absence of a material capable of releasing or of being associated with an odor may be inferred through the detection of the odor itself. Unlike other detecting apparatus such as gas chromatography, liquid chromatography, mass spectrometry, and others, which separate individual chemical species from a sample whole and analyze each individual specie as to identity and quantity, the detection apparatus and methods of the present invention detect odor as a whole. In this regard, the detection process is similar to mammalian olfaction in that simultaneous, in discriminate response to the entirety of odor molecules present in a sample is accomplished.

As indicated previously, the response of an individual dielectric material will vary with the identity and quantity odor molecules adsorbed thereupon. Similarly, the response engendered by a particular odor molecule may differ with differing dielectric materials. By judicious selection of dielectric material and, optionally, by proper selection of adsorbant species for adsorbtion of interfering, low molecular weight materials from the carrier gas flow, particularized responses of the apparatus in accordance with the methods of this invention may be obtained which are "tuned" to a particular environment or for a particular analytical format. As will be appreciated by one skilled in the art, odor detectors for particular uses may be developed such as, for the detection of spoilage in meats, fish, or other foodstuffs, or for the detection of disease or other states in animals, especially mammals or in plants. Through this "tuning" process, ddetectors having improved response may be devised.

The apparatus and methods in accordance with the present invention may be used in techniques which have heretofore been amenable for analysis only through chromatographic or spectrometric analysis. Examples of such fields wherein use of these apparatus and materials is likely to be successful may be found in, for example, "Determination of Trace Organics in Air and Water", Mieure et al., Journal of Chromatagraphic Science, Vol 11, pp. 559–570 (1973); "Salivary Volatiles as Indicators of Periodontitis", Kostelc et al., Journal of Periodontal Research, Vol. 15, pp. 1185–1192 (1980); "The Chemistry of Aroma", Parliament, Chemtech, Vol 9, pp. 284–289 (1980); "The Role of Organic Volatile Profiles in Clinical Diagnosis", Zlatkis, Clinical Chemistry, Vol 27, pp. 789–797 (1981); and "Head Space Analysis of Volatile Metabolites of *Pseudomonas aeruginosa* and Related Species by Gas Chromatography-Mass Spectrometry", Labows et al., Journal of Clinical Microbiology, pp. 521–526 (1980).

A particular use for which the present apparatus and methods show promise is in the area of analysis of subsurface geologic structure for the presence or absence of odor. In this regard, the employment of a dynamic electro-odocell in connection with penetrometer sample collector for analyzing subsurface odor was disclosed, in confidence, to the Fugro Gulf Company of Houston, Tex. in April of 1981. No use, sale or non-confidential disclosure of this or any other embodiment of this invention has yet been made, however.

Those skilled in the art will readily appreciate that numerous other uses for the methods and apparatus of the present invention are contemplated that all such uses are deemed to be within the spirit of this invention. The following examples are intended as illustrative only and are not to be construed as limiting the scope of the present invention.

EXAMPLE 1

An odor detection apparatus generally in accordance with FIG. 1 was employed to determine the change in dielectric potential and the resulting curve of potential versus time for various odor materials on a regenerated cellulose dielectric membrane. A substantially uniform flow of nitrogen gas (50 ml/min) was transmitted through a regenerated cellulose membrane supported by a stainless steel mesh. The stainless stel mesh was electrically connected to a preamplifier and an X-Y recorder. The membrane was produced by Gelman Sciences Inc. and denominated A 450. It was said to be Alpha Metricel, a form of regenerated cellulose having pore sizes on the order of 0.45 m. Two ml of each sample to be tested was injected into an entrainment apparatus similar to that depicted schematically in FIG. 1. The material was allowed to stand for 5 minutes at room temperature to allow head space equilibrium to occur.

Figure 3:
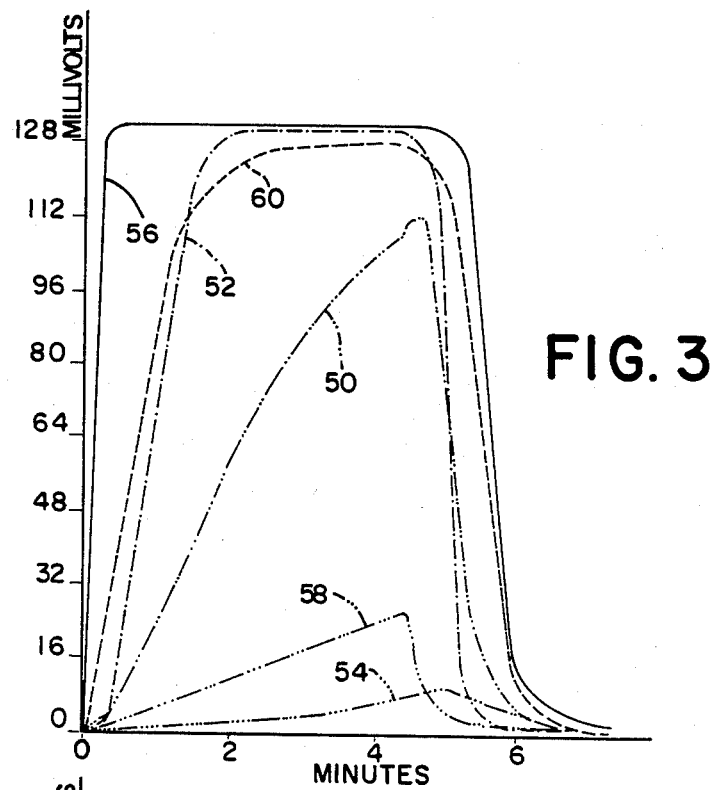
FIGS. 3-6 are detection curves representing changes in dielectric potential with time of various odorous materials in accordance with this invention.

The flow of nitrogen gas was then diverted to perfuse the head space thus to entrain the vaporous sample and to cause it to transit the detector including the dielectric membrane. Perfusion of the head space was continued for 2 minutes at which time flow to pure nitrogen flow was resumed until the dielectric potential had returned to its dynamic equilibrium value in the nitrogen flow. A graphic representation of dielectric potential versus time was made for each of the samples tested; these representations are presented in FIG. 3. The material tested were ethyl alcohol 50, methyl alcohol 52, ammonia 54, Dimethyl disulfide 56, benzene 58, and chloroform 60.

EXAMPLE 2

Figure 4:
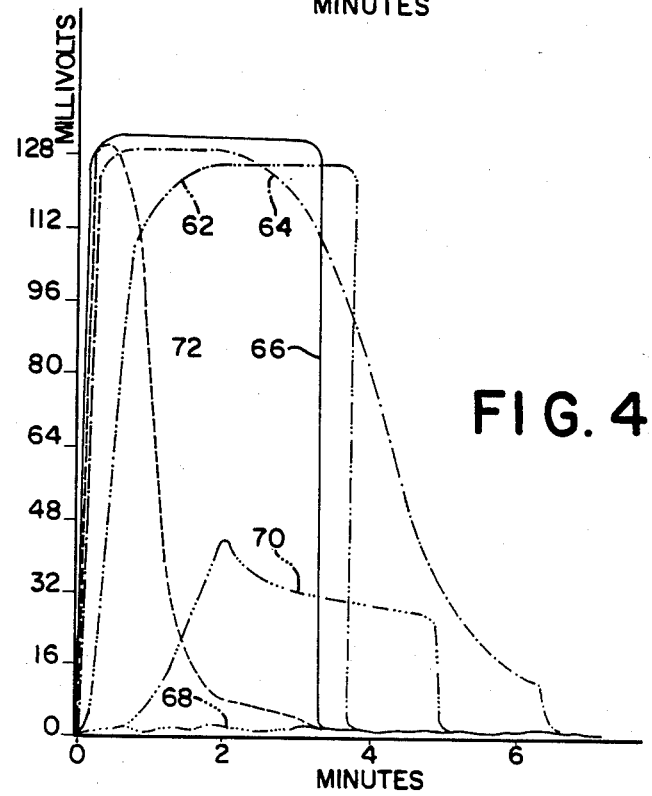

The general procedure of Example 1 was employed with a cellulose acetate/nitrate membrane supplied by the Millipore Corporation having pore sizes of approximately 0.22 m. FIG. 4 depicts the detector response curves obtained for the samples ethyl alcohol 62, acetone 64, methanol 66, pyridine 68, ammonia 70, and a 1 mg/ml prepared vapor sample of Dimethyl disulfide in nitrogen 72.

EXAMPLE 3

Figure 5:
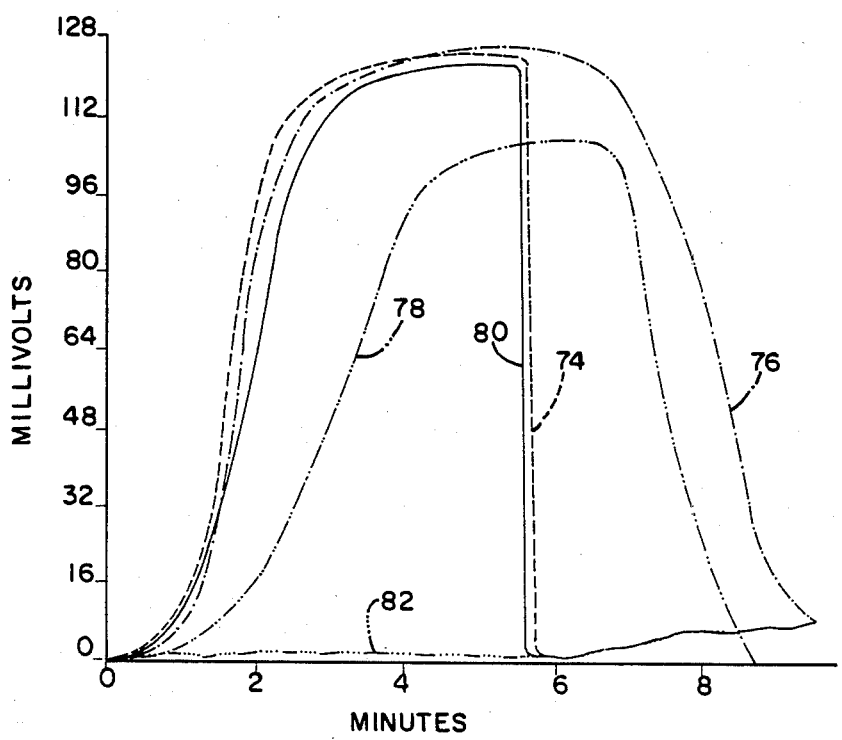

The procedure of Example 1 was generally followed employing Gelman membrane A450 as related in that Example. Limonene together with various fruits containing limonene in their odor profile were analyzed. One whole piece of each fruit was placed in a plastic container simulating a small travelers' bag and allowed to stand at room temperature for approximately 30 minutes to volatilize the odiferous components present therein. The head space was then flushed with nitrogen as before for a period of two minutes at which time the carrier gas was caused to by-pass the head space. The odor profiles for each fruit tested are presented in FIG. 5. Limonene 74, papaya 76, grapefruit 78, orange 80, and a distilled water control 82 were each analyzed.

EXAMPLE 4

Figure 6:
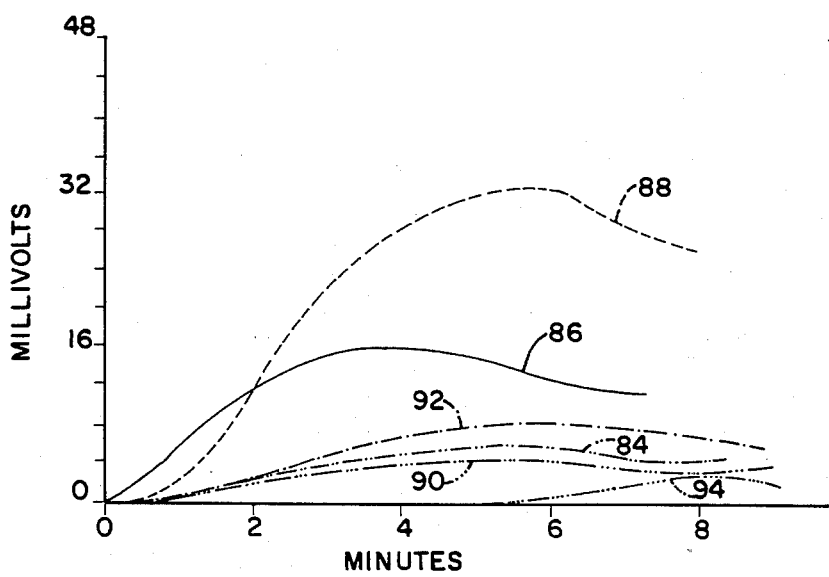

The general procedure of Example 1 was followed employing Gelman membrane AN800 having a pore size of about 0.80 m. A flow of 200 ml/min of nitrogen was employed in this Example. The sample container was charged with the indicated micro-organisms and 50 ml of trypticase soy agar nutrient broth-medium placed in the sample container. The brew was allowed to stand for 30 minutes in order to saturate the head space with volatile products. After initial equilibration of the dielectric potential of the membrane in the nitrogen gas flow, the head space was perfused with the nitrogen flow for two minutes after which time reversion to pure nitrogen was accomplished. The dielectric potential versus time curve of the membrane is presented in FIG. 6. The micro-organisms tested included a blank, representing the TSA growth medium 84, *Pseudomonas aeruginosa* 86, *Staphylococcus aureus* 88, *Corynebacterium bovis* 90, *Candida albicans* 92, and *Microsporum canus* 94.

What is claimed is:

1. An apparatus for the detection of odor comprising:
   dielectric sensing means having a dielectric potential responsive to odor molecules adsorbed onto said sensing means, said sensing means being at least partially permeable to flow of gas,
   carrier gas flow means for directing a substantially uniform flow of carrier gas into contact with and through said sensing means, and
   means for detecting the dielectric potential of said sensing means.

2. The apparatus of claim 1 wherein said sensing means comprises a membrane.

3. The apparatus of claim 1 comprising a plurality of sensing means.

4. The apparatus of claim 1 wherein said detection means detects changes in said potential with time.

5. The apparatus of claim 4 wherein said detection is graphically displayable.

6. The apparatus of claim 1 further comprising an electrically conductive support in contact with said sensing means.

7. The apparatus of claim 1 further comprising electrically conductive grounding means in contact with said sensing means.

8. The apparatus of claim 1 further comprising means for removing from said flow at least a portion of low molecular weight molecules present in said flow.

9. The apparatus of claim 1 further comprising means for entraining a vaporous sample in said flow.

10. The apparatus of claim 1 wherein said flow means comprises means for applying a vacuum.

11. The apparatus of claim 1 further comprising means for digitizing said detected dielectric potential.

12. A method for detecting odor comprising:
    providing a dielectric sensing means having a dielectric potential responsive to odor molecules adsorbed onto said sensing means, said sensing means being at least partially permeable to flow of gas,
    contacting said sensing means with a substantially uniform flow of a carrier gas by passing the gas through the sensing means, and
    detecting the dielectric potential of said sensing means.

13. The method of claim 12 wherein said sensing means comprises a membrane.

14. The method of claim 12 wherein a plurality of sensing means is provided.

15. The method of claim 12 wherein said detecting measures said potential over a period of time.

16. The method of claim 15 wherein said detection is displayed graphically.

17. The method of claim 12 further comprising entraining in said flow a vaporous sample.

18. The method of claim 12 wherein said flow is contacted with a means for removing at least a portion of low molecular weight molecules from said flow prior to contacting said sensing means.

19. The method of claim 12 further comprising digitizing said detected electric potential.

20. A method for identifying an odor comprising:
    contacting a dielectric sensing means having a dielectric potential responsive to odor molecules adsorbed onto said sensing means, said sensing means being at least partially permeable to flow of gas with
    a substantially uniform flow of a carrier gas by passing the gas through the sensing means,
    entraining in said flow at least one vaporous sample of a known odorous sample,
    detecting the dielectric potential of said sensing means over a period of time subsequent to said entrainment to provide a curve of said dielectric potential with time,
    separately entraining in said flow a vaporous sample of unknown composition,
    detecting the dielectric potential of said sensing means over a period of time subsequent to said separate entrainment to provide a curve of said dielectric potential; and comparing the curve of the known sample with the curve of the sample of unknown composition.

21. The method of claim 20 wherein each of said curves are graphically displayed.

22. The method of claim 21 wherein said comparing is of the graphs thus displayed.

23. The method of claim 20 wherein said curves are digitized.

24. The method of claim 20 wherein said contacting is at least partially via permeation of said sensing means.

* * * * *